United States Patent
Englert et al.

(10) Patent No.: US 11,306,116 B2
(45) Date of Patent: Apr. 19, 2022

(54) METHOD FOR SEPARATING NATURAL SUBSTANCE MIXTURES BY MEANS OF SCPC

(71) Applicant: SPECTRUM THERAPEUTICS GMBH, Neumarkt (DE)

(72) Inventors: Michael Englert, Nuremberg (DE); Andreas Ruiz, Dornhausen (DE)

(73) Assignee: Spectrum Therapeutics GMBH, Neumarkt (DE)

( * ) Notice: Subject to any disclaimer, the term of this patent is extended or adjusted under 35 U.S.C. 154(b) by 0 days.

(21) Appl. No.: 16/613,546

(22) PCT Filed: May 29, 2018

(86) PCT No.: PCT/EP2018/064121
§ 371 (c)(1),
(2) Date: Nov. 14, 2019

(87) PCT Pub. No.: WO2018/233991
PCT Pub. Date: Dec. 27, 2018

(65) Prior Publication Data
US 2021/0230206 A1     Jul. 29, 2021

(30) Foreign Application Priority Data
May 29, 2017  (EP) .................... 17173304

(51) Int. Cl.
| | | |
|---|---|---|
| *C07C 7/10* | (2006.01) | |
| *C07C 37/72* | (2006.01) | |
| *B01D 15/00* | (2006.01) | |
| *C07H 17/04* | (2006.01) | |
| *B01D 15/18* | (2006.01) | |
| *B01D 15/30* | (2006.01) | |
| *C07D 311/64* | (2006.01) | |
| *C07D 311/78* | (2006.01) | |

(52) U.S. Cl.
CPC ......... *C07H 17/04* (2013.01); *B01D 15/1892* (2013.01); *B01D 15/30* (2013.01); *C07C 7/10* (2013.01); *C07C 37/72* (2013.01); *C07D 311/64* (2013.01); *C07D 311/78* (2013.01)

(58) Field of Classification Search
CPC ....... C07C 7/10; C07C 37/72; B01D 15/1892; B01D 15/30
See application file for complete search history.

(56) References Cited

FOREIGN PATENT DOCUMENTS

EP     3061510     8/2016

OTHER PUBLICATIONS

Goll et al. "Study of the separation limits of continuous solid support free liquid-liquid chromatography: Separation of capsaicin and dihydrocapsaicin by centrifugal partition chromatography," Journal of Chromatography A, Feb. 2013, vol. 1284, pp. 59-68.
Pedan et al. "Extraction of cocoa proanthocyanidins and their fractionation by sequential centrifugal partition chromatography and gel permeation chromatography," Analytical and Bioanalytical Chemistry, Jun. 2016, vol. 408, No. 21, pp. 5905-5914.
Translated International Search Report for International (PCT) Patent Application No. PCT/EP2018/064121, dated Sep. 19, 2018, 3 pages.
International Search Report and Written Opinion for International (PCT) Patent Application No. PCT/EP2018/064121, dated Sep. 19, 2018, 10 pages.

*Primary Examiner* — Sikarl A Witherspoon
(74) *Attorney, Agent, or Firm* — Sheridan Ross P.C.

(57) ABSTRACT

The invention relates to a method for separating natural substance mixtures, in particular those consisting of plant extracts, and for isolating and purifying and obtaining same, by means of sequential centrifugal partition chromatography (sCPC).

19 Claims, 14 Drawing Sheets

METHOD FOR SEPARATING NATURAL SUBSTANCE MIXTURES BY MEANS OF SCPC

CROSS REFERENCE TO RELATED APPLICATIONS

This application is a national stage application under 35 U.S.C. 371 and claims the benefit of PCT Application No. PCT/EP2018/064121 having an international filing date of 29 May 2018, which designated the United States, which PCT application claimed the benefit of European Patent Application No. 17173304.1 filed 29 May 2017, the disclosures of which are incorporated herein by reference in their entirety.

The invention relates to a method for separating natural substance mixtures, especially those from plant extracts and the isolation and purification thereof as well as extraction using Sequential Centrifugal Partition Chromatography (sCPC).

As a counterflow method, the continuous TMB (True Moving Bed) process combines the advantages of liquid-liquid chromatography with those of a continuous process, such as the SMB (Simulated Moving Bed) using a centrifugal column or a rotating separating column. Liquid-liquid chromatography works with both a liquid mobile phase and a liquid stationary phase, and no solid column material is used. In contrast to the SMB and its related processes, in a TMB the movement of the immiscible phases is not achieved via a valve circuit, but rather via a clocked phase reversal at a selected frequency. The underlying technical teaching is disclosed in WO 2005/011835 A1.

A characteristic feature is the continuous change of the stationary phase to the mobile phase and vice versa, i.e. the denser or less dense phase can be selected as the mobile phase and a change of this selection is possible during a separation. This preparative chromatography is therefore referred to as "Sequential Centrifugal Partition Chromatography (sCPC)". Due to a different distribution coefficient, the substances A and B to be separated are moved in a liquid-liquid centrifugal column at different velocities in the two phases having different densities.

An sCPC apparatus comprises at least one rotor having many round metal plates in which, for example, more than one thousand series-connected separation chambers are located (also referred to as rotor chambers, when forming a rotating separating column). With the aid of a pump, a mobile liquid phase (continuously) flows through the stationary liquid phase in the rotor. The rotor is accelerated to approx. 1,000 rpm and more, for example, so that, as a result of the density differences in the individual chambers, the centrifugal force causes the separation of the two liquid phases. As soon as the liquid mobile phase is in equilibrium with the liquid stationary phase, the sample or the substance mixture can be injected into the rotor.

The substance separation takes place as a result of differing adsorption in the mobile or stationary phase or the respective distribution coefficient (K) of a substance to the mobile/stationary phase, wherein the substances are moved through the individual separation chambers to the rotor outlet and fractionated. The characteristic alternating change of the stationary phase and the mobile phase takes place by controlling the used pumps with the aid of valves in a frequency to be selected. In a period of time to be selected (duration of pumping, pump duration), the associated solvent is pumped into the respectively driven phase, namely in each case at the two ends of a rotor, so that the pumps are oppositely disposed.

The sample or the substance mixture is preferably fed into the middle of the rotor. In a further embodiment, two or more rotors can be coupled.

A principal cycle is shown in FIG. 1.

The rotor chambers are preferably filled with an upper and a lower liquid phase in a 50/50 ratio (volume %). The substance mixture is continuously fed between the two rotating separating columns with the aid of a pump at a defined flow rate and the separation takes place in a cyclical and time-delayed manner, whereby, in a first step, the upper phase serves as the mobile phase (ascending) and, in a second step, the lower phase serves as the mobile phase (descending).

In accordance with the concentration and the different distribution coefficients of the substances in the substance mixture, the separation takes place in two product streams, see FIG. 1. Suitable devices and equipment can be obtained from Armen Technologies (France) under the name "True Moving Bed CPC".

With respect to sCPC, the state of the art describes the purification of model substances and binary mixtures (Johannes Goll, Andreas Frey, and Mirjana Minceva. "Study of the separation limits of continuous solid support free liquid-liquid chromatography: Separation of capsaicin and dihydrocapsaicin by centrifugal partition chromatography", Journal of Chromatography A 1284 (2013): 59-68; Hopmann E, Goll J, Minceva M. "Sequential centrifugal partition chromatography: A new continuous chromatographic technology", Chem Eng Technol. 2012; 35 (1): 72-82, here: binary mixture of capsaicin and dihydrocapsaicin), but not methods for separating and/or purifying natural substances from plant extracts, namely for the production of fractions and pure substances.

The invention therefore relates to a method for separating and/or purifying natural substances from plant extracts, comprising at least one liquid-liquid partition chromatography step, wherein a continuous change of the stationary phase to the mobile phase and vice versa takes place (sCPC), wherein one or more fractions are removed.

The invention therefore relates to a method for separating and/or purifying natural substances from plant extracts, comprising at least one liquid-liquid partition chromatography step, wherein a continuous change of the stationary phase to the mobile phase and vice versa takes place (sCPC), wherein at least one pure substance is removed.

In the context of this invention, a "plant extract" is a multicomponent mixture of natural substances, which contains more than two natural substances, in particular more than 10 or 100 natural substances, in particular more than 200, 300, 500 or 1,000 natural substances. Plant extracts can be obtained from plant materials, for example by extraction, percolation or maceration. Solvents such as water, C1-C5 alcohols, ethanol, or other solvents having sufficient polarity can be used as extractants. A common extraction is, for example, a mixture of water/ethanol (50:50, 70:30, 30:70) at 70 degrees Celsius. Further preferred according to the invention are plant extracts containing less than 50 wt % or 40 wt % fats or lipids, in particular less than 20 wt % or 10 wt % fats or lipids, because fats lead to an impairment of the separation efficiency in the sCPC process.

According to the invention, the following genera are preferred for plant extracts:

*Equiseti, Juglandis, Millefolii, Quercus, Taraxaci, Althaeae, Matricariae, Centaurium, Levisticum, Rosmari-* nus, *Angelica, Artemisia, Astragalus, Leonurus, Salvia, Saposhnikovia, Scutellaria, Siegesbeckia, Armoracia, Capsicum, Cistus, Echinacea, Galphimia, Hedera, Melia, Olea, Pelargonium, Phytolacca, Primula, Salix, Thymus, Vitex, Vitis, Rumicis, Verbena, Sambucus, Gentiana, Cannabis, Silybum.*

According to the invention, the following species are preferred for plant extracts:

*Equiseti herba* (horsetail), *Juglandis folium* (walnut leaf), *Millefolii herba* (yarrow), *Quercus cortex* (oak bark), *Taraxaci herba* (dandelion), *Althaeae radix* (marshmallow root) and *Matricariae flos* (or *Flos chamomillae* (chamomile)), *Centaurium erythraea* (centaury), *Levisticum officinale* (lovage), *Rosmarinus officinalis* (rosemary), *Angelica dahurica* (Dahurian angelica, Pinyin name: Bai Zhi), *Angelica sinensis* (Chinese *angelika*, Pinyin name: Dang Gui), *Artemisia scoparia* (*capillary wormwood*, Pinyin name: Yin Chen), *Astragalus membranaceus* (var. *Mongolicus*) (*Mongolian milkvetch*, Chin.: Huang-Qi), *Leonurus japonicus* (*Oriental motherwort*, Chin.: T'uei), *Salvia miltiorrhiza* (red sage, Chin.: Danshen), *Saposhnikovia divaricata* (siler, Pinyin name: Fang Feng), *Scutellaria baicalensis* (Baikal skullcap, Ban Zhi Lian), *Siegesbeckia pubescens* (*Siegesbeckia herb*, Pinyin name: Xi Xian Cao), *Armoracia rusticana* (horseradish), *Capsicum* sp. (pepper), *Cistus incanus* (hoary rock-rose), *Echinacea angustifolia* (narrow-leaved purple coneflower), *Echinacea purpurea* (purple coneflower), *Galphimia glauca, Hedera helix* (ivy), *Melia toosendan* (Chinese elderberries, Chin.: Chuan Lian Zi), *Olea europaea* (olive), *Pelargonium* sp. (*pelargonia*), *Phytolacca americana* (pokeweed), *Primula veris* (cowslip), *Salix* sp. (willow), *Thymus* L. (thyme), *Vitex agnus castus* (chasteberry), *Vitis vinifera* (common grape vine), *Rumicis herba* (sorrel herb), *Verbena officinalis* (*Verbena*), *Sambucus nigra* (black elder), *Gentiana lutea* (yellow gentian), *Cannabis sativa* (hemp), *Silybum marianum* (milk thistle).

Mixtures of the aforementioned genera and/or species are likewise included in the invention.

The abovementioned species and genera are particularly rich in healing natural substances and are described as medicinal plants, for example as in the plant extract-based products of Bionorica SE (e.g. Bronchipret®, Imupret®, Sinupret®). These types of plants furthermore contain typical characteristic substance classes of natural substances, such as secondary metabolites such as flavonoids, polyphenols, etc. These types of medicinal plants are used in the preparation of medicinal products.

In a preferred embodiment, the plant extract is obtained from a first solvent such as alcohols, ethanol, water, hydrocarbons, heptane or mixtures thereof, and the soluble components are used in the method according to the invention (hereinafter and above: substance mixture).

For the method for separating and/or purifying natural substances from plant extracts using sCPC according to the invention, the critical process parameters, namely the flow rate of the upper phase, the flow rate of the lower phase, the substance mixture flow rate, the descending cycle time and the ascending cycle time, are preferably implemented in accordance with the following steps:

Setting a defined concentration of the substance mixture in the selected solvent system;

Setting the maximum flow rate for the lower and the upper phase at which no uncontrolled phase bleeding of the liquid phases takes place;

Setting the maximum substance mixture flow rate;

Adjusting the cycle time of the descending and/or ascending mode to shift the intersection point of the separation in the chromatogram between different substances as needed; short switching times are preferably used to prevent uncontrolled phase bleeding and leakage of unseparated substances.

This procedure allows the selective enrichment and depletion, as well as the separation, of fractions or pure substances, such as, but not limited to, cannabidiol, tetrahydrocannabinol, casticin, gentiopicroside, agnuside, chamazulene, primulasaponin 1, etc.

These substance classes of plant extracts, such as alkaloids, bitter compounds, anthocyanins, anthraquinones, coumarins, flavonoids, glucosinolates, lactones, lignans, lipids, cannabinoids, phenols, polyphenols, saponins, terpenes, xanthones, for example, can be enriched or depleted in the fractions, which can be removed.

Such fractions and pure substances can particularly advantageously be obtained in high purity and yield.

Solvents that can be used in the liquid-liquid partition chromatography can, for example, be found in Skalicka-Wozniak K, Garrard I, A comprehensive classification of solvent systems used for natural product purifications in countercurrent and centrifugal partition chromatography, Nat Prod Rep. 2015 November; 32(11):1556-61.

According to the invention, examples of suitable solvents from which two-phase solvent systems (mobile phase/stationary phase) can be provided for plant extracts are:

a.) hydrocarbons such as n-hexane, cyclohexane, isohexane, heptane, isooctane;

b.) ethers such as t-butyl methyl ether, petroleum ether, diethyl ether;

c.) halogenated solvents such as chloroform, dichloromethane, benzotrifluoride, dichloroethane, tetrachloromethane, trichloroethane;

d.) water soluble alcohols such as butanol, methanol, ethanol, isopropanol;

e.) water soluble esters such as ethyl acetate, isopropyl acetate;

f.) acetonitrile, toluene.

Suitable two-phase solvent systems can be produced from the aforementioned solvents, preferably such as, in particular at least containing:

n-heptane and/or acetonitrile, n-heptane/acetonitrile n-heptane/ethyl acetate/acetonitrile;

n-heptane/ethyl acetate/t-butyl methyl ether/acetonitrile;

n-heptane/ethyl acetate/methanol/water;

n-heptane/ethanol/water.

The invention therefore also relates to a method for separating and/or purifying natural substances from plant extracts including at least one liquid-liquid partition chromatography step, in which a continuous change of the stationary phase to the mobile phase and vice versa takes place, and both the stationary phase and the mobile phase are selected from at least two solvents of the group of hydrocarbons having 5-8 carbon atoms, in particular n-heptane, acetonitrile, ethyl acetate, t-butyl methyl ether, alcohols, in particular methanol, water, ethanol, n-heptane and/or acetonitrile, so that a two phase system can be obtained.

Particularly preferred, however, are n-heptane and/or acetonitrile for separating the plant extracts using the sCPC method according to the invention. For an optimal separation of the plant extracts, it is furthermore preferred that the rotor is accelerated to a rotation of more than 2,000 rpm, in particular 2,500 rpm and more, to carry out the method according to the invention.

The following examples and figures serve only to explain the invention without limiting the invention to said examples.

EXAMPLE 1

Description of Equipment

Equipment:

Continuous liquid-liquid chromatography True Moving Bed (TMB) 500 system, with a 2×250 mL rotor, 100-3,000 rpm speed, up to 100 mL/min flow rate, 100 bar maximum pressure of Armen Instrument (Saint-Ave, France) or 12 L production system with a 2×6 L rotor.

Additional Equipment: 2× eluent pump, up to 100 mL/min flow rate; 2× sample delivery pump, up to 50 mL/min flow rate; 2× diode array detector Ecom, 4 wavelengths, 200-600 nm detection range, 6 kg; 2× fraction collector LS-5600, incl. rack set made of stainless steel, 20 kg Operating Principle:

The sample or substance mixture is injected continuously onto both rotors in phases, and the sample components are separated according to their polarity and their liquid-liquid distribution coefficients K using a suitable two-phase solvent system. After the system is started, a stationary, steady state is established. Product side A can then be removed at one rotor by means of a fraction collector. Alternately, product side B can be removed at the second rotor by mean of a further fraction collector. The detectors are used to monitor the separation.

EXAMPLE 2

Industrial Hemp Extract with Depletion of THC

Extraction of Industrial hemp extract THC-free: Extraction of *Cannabis* herb using $CO_2$, decarboxylation at 120° C. in a vacuum, dissolution in n-heptane/ethanol/water, Method:

Parameters:

| | |
|---|---:|
| Rotation: | 2,600 rpm |
| Ascending mode: | |
| Flow rate elution: | 30 mL/min |
| Flow rate injection: | 10 mL/min/5 mL/min |
| Pump duration: | 90 sec |
| Descending mode: | |
| Flow rate elution: | 30 mL/min |
| Flow rate injection: | 10 mL/min/5 mL/min |
| Pump duration: | 99 sec |

Flow rate = flow rate

Figure 1:
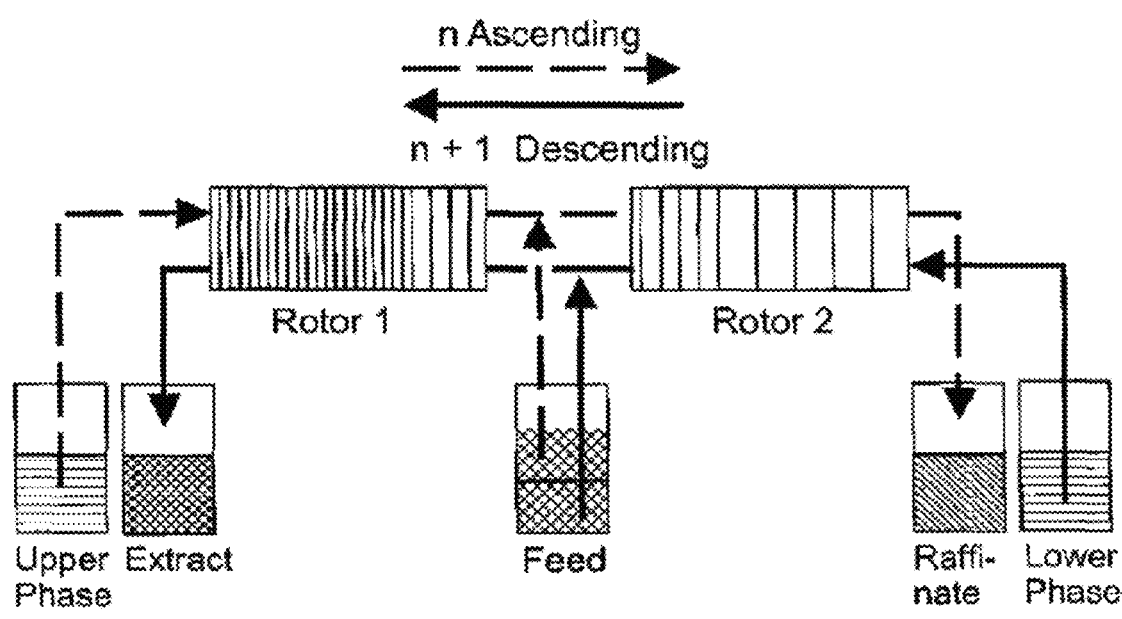
FIG. 1 shows a principal cycle for an sCPC.
Figure 2:
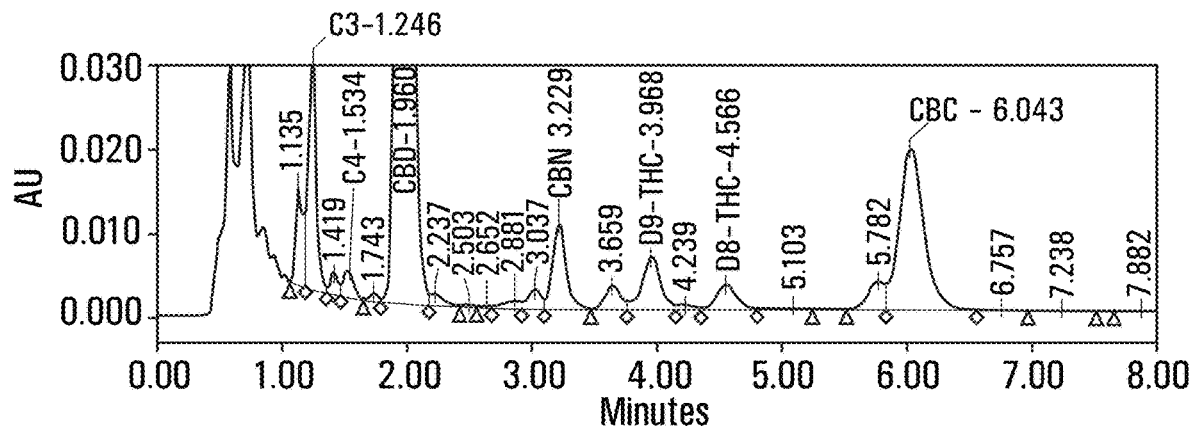
FIG. 2 shows an HPLC chromatogram for the starting material as described in Example 2.

HPLC Chromatogram Starting Material (see FIG. 2):

Content analysis: CBD: 51.54%, D9-THC: 1.21%, CBN: 1.38%

Figure 3:
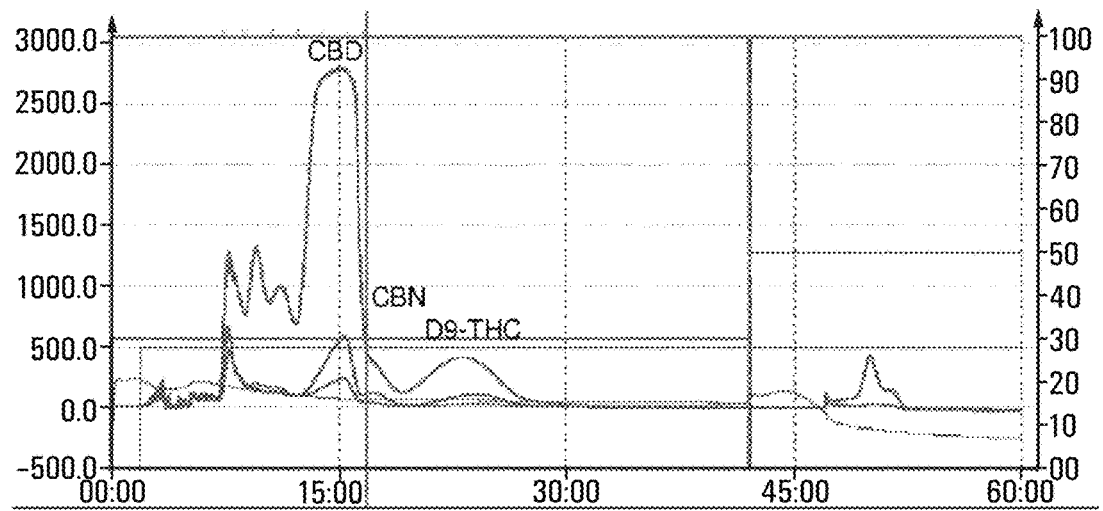
FIG. 3 shows the Batch partition chromatography (CPC) as described in Example 2.

Batch Partition Chromatography (CPC) (see FIG. 3):

Separation of 3.05 g starting product (50 g/L) in 30 min in batch operation with n-heptane/ethanol/water (5:4:1.4)—the vertical line at 17:00 describes the separation line in the later continuous partition chromatography.

Figure 4:
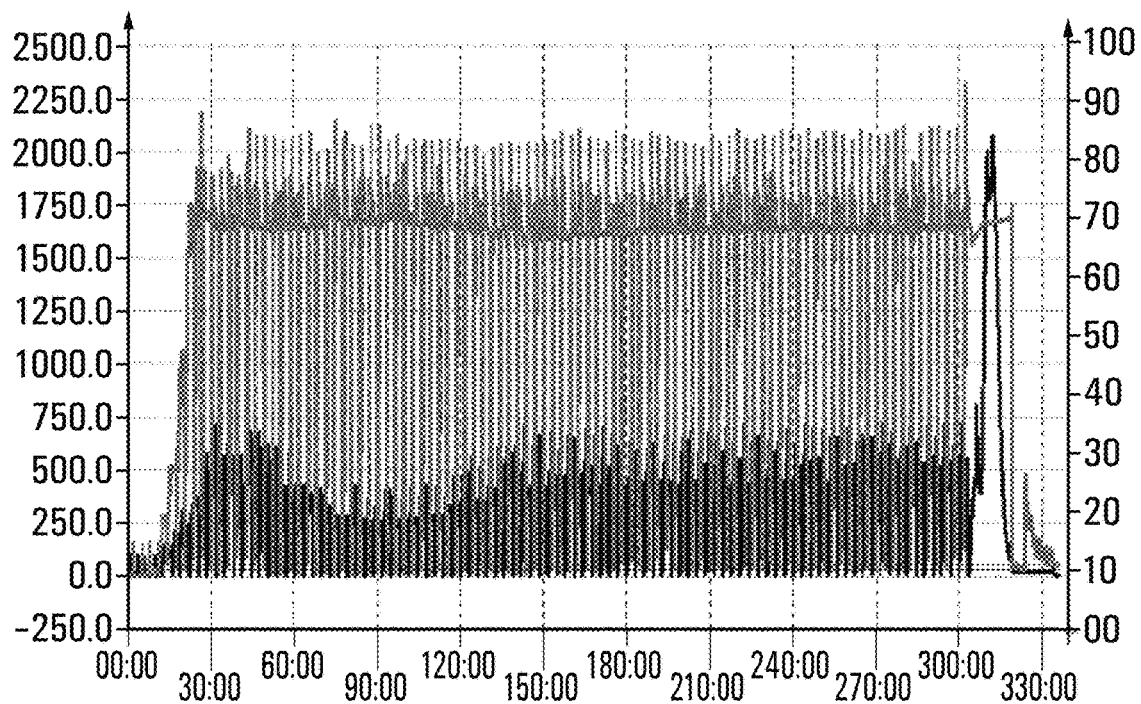
FIG. 4 shows the Continuous Partition Chromatography (sCPC) as described in Example 2.

Continuous Partition Chromatography (sCPC)(see FIG. 4):

Separation in continuous operation (50 g/L) with the sCPC with n-heptane/ethanol/water (5:4:1.4)

Grey: UV signal descending side, black: UV signal ascending side

Figure 5:
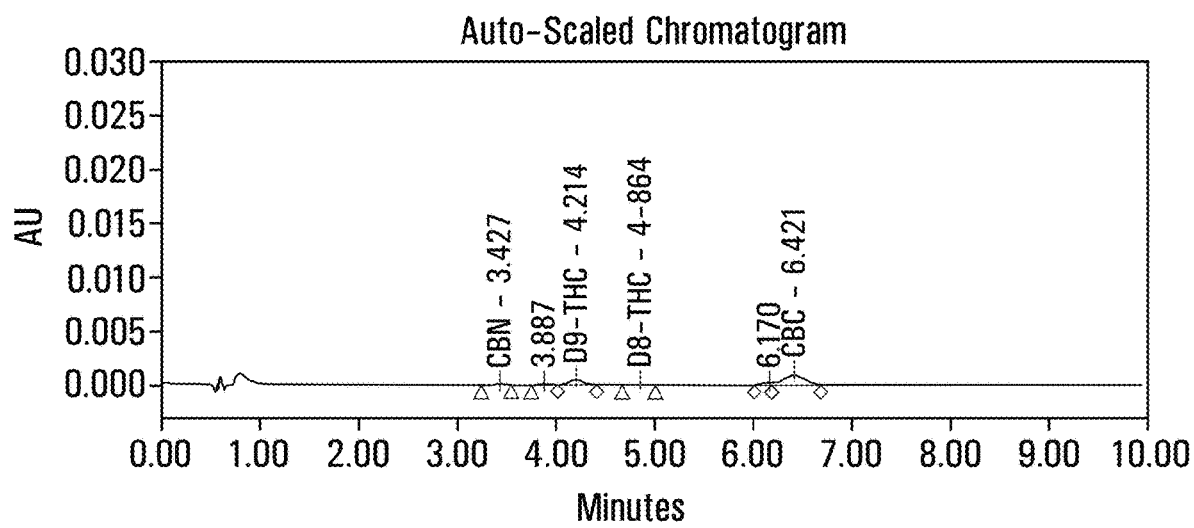
FIG. 5 shows the HPLC chromatogram of the ascending side as described in Example 2.
Figure 6:
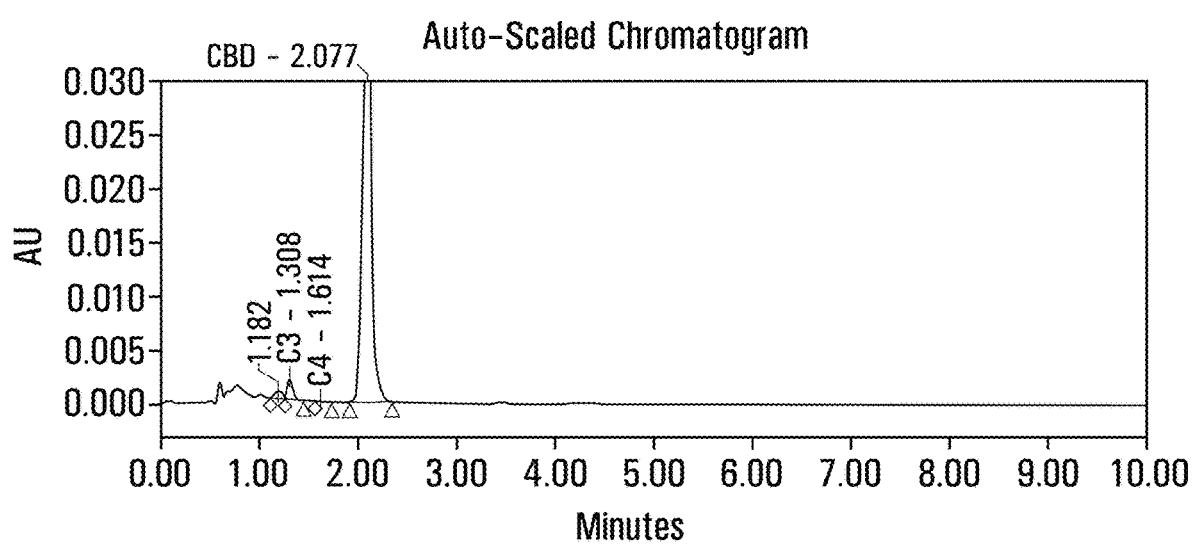
FIG. 6 shows the HPLC chromatogram of the descending side as described in Example 2.

HPLC chromatogram of the ascending side (see FIG. 5):

Content analysis: CBD: 0.00%, D9-THC: 2.63%, CBN: 2.84% HPLC chromatogram of the descending side (see FIG. 6):

Content analysis: CBD: 96.22%, D9-THC: 0.00%, CBN: 0.00%

Comparison of the productivities for industrial hemp extract separation:

| System | Mass flow [g/h] | Solvent consumption [L/h] | Consumption per g Product [L/g] |
|---|---|---|---|
| Continuous True Moving Bed 2 × 250 mL rotor | 34.81 | 8.1 | 0.23 |
| Batch CPC 500 mL rotor | 6.10 | 1.8 | 0.30 |

EXAMPLE 3

Purification of Casticin

Parameters:

| Rotation: | 2,600 rpm |
|---|---|
| Ascending mode: | |
| Flow rate elution: | 15 mL/min |
| Flow rate injection: | 5 mL/min |
| Pump duration: | 30 sec |
| Descending mode: | |
| Flow rate elution: | 15 mL/min |
| Flow rate injection: | 5 mL/min |
| Pump duration: | 60 sec |

Figure 7:
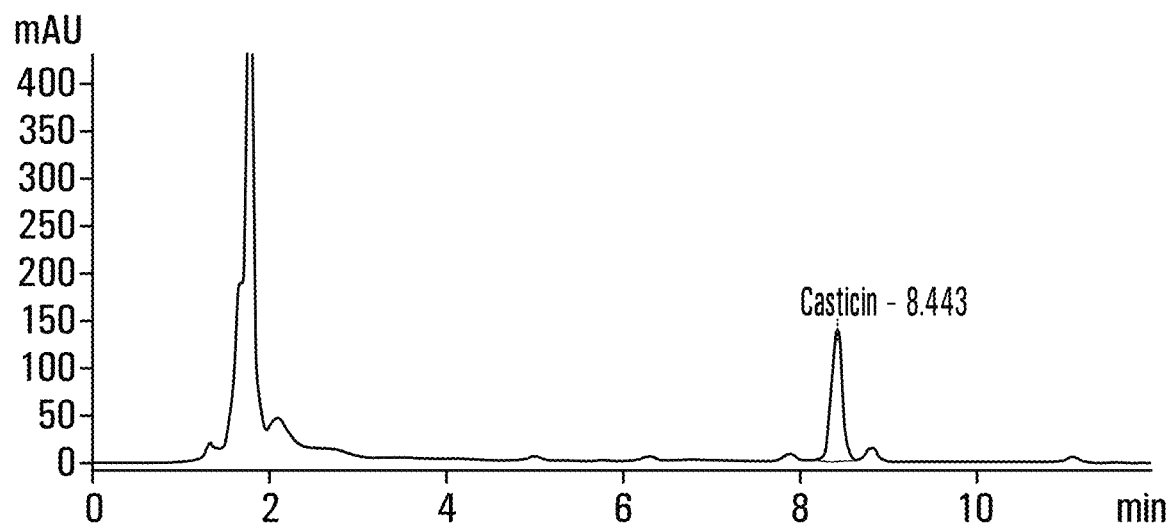
FIG. 7 shows an HPLC chromatogram for the starting product Essi Agni casti as described in Example 3.

HPLC Chromatogram Starting Product Essi Agni casti (see FIG. 7):

Solvent system: n-heptane/ethanol/water (5:4:1) (v/v/v)

Content of casticin in the dry extract: 0.145% (m/m)

Figure 8:
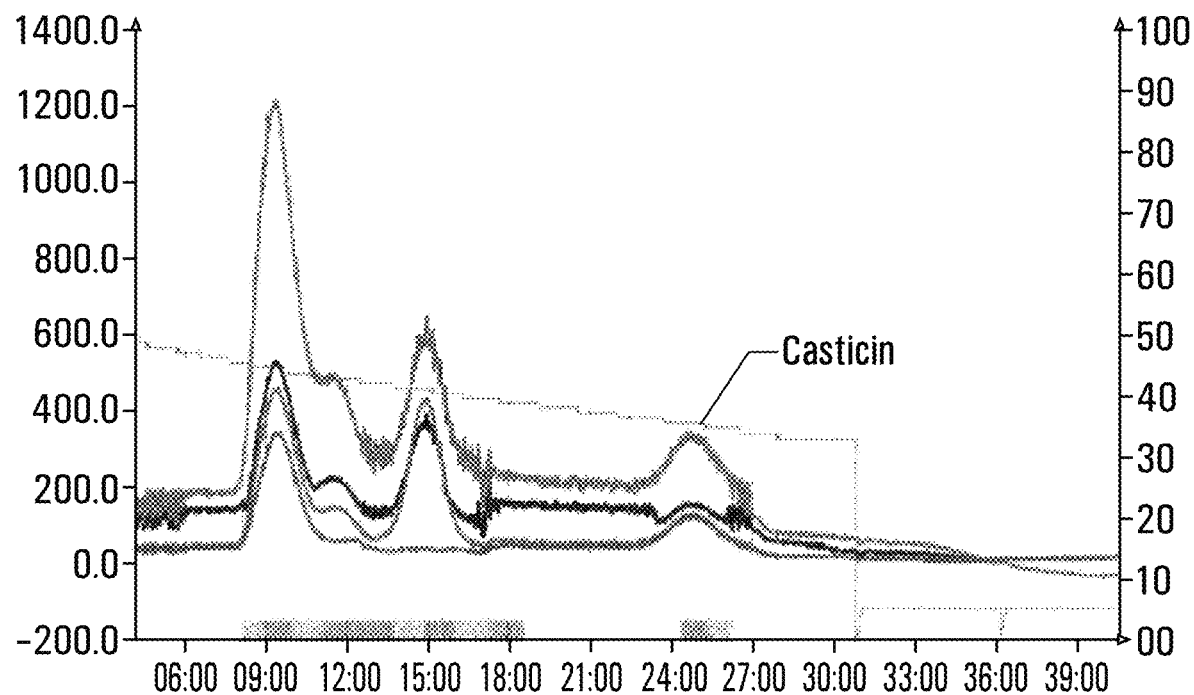
FIG. 8 shows the Batch partition chromatography (CPC) as described in Example 3.

Batch partition chromatography (CPC) (see FIG. 8):

Separation of 1 g Essi Agni casti in batch operation with n-heptane/ethyl acetate/ethanol/water (7:10:7:10)—the vertical lines at 22:00 and 28:00 describe the separations in the later continuous partition chromatography.

Figure 9:
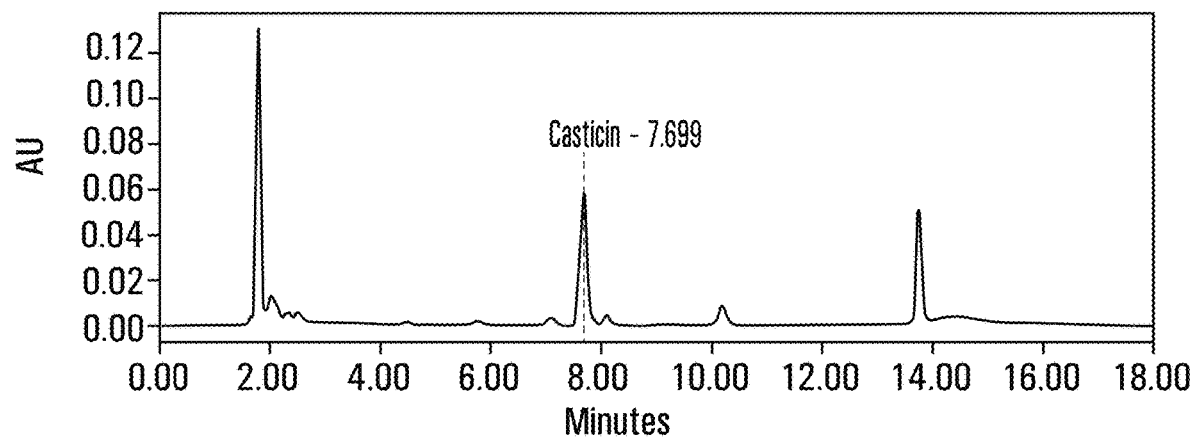
FIG. 9 shows a chromatogram for True Moving Bed (TMB) Purification Step 1 for Pre-enrichment as described in Example 3.

True Moving Bed Purification Step 1 for Pre-enrichment (see FIG. 9):

Content of casticin: 60.3% (m/m)

Figure 10:
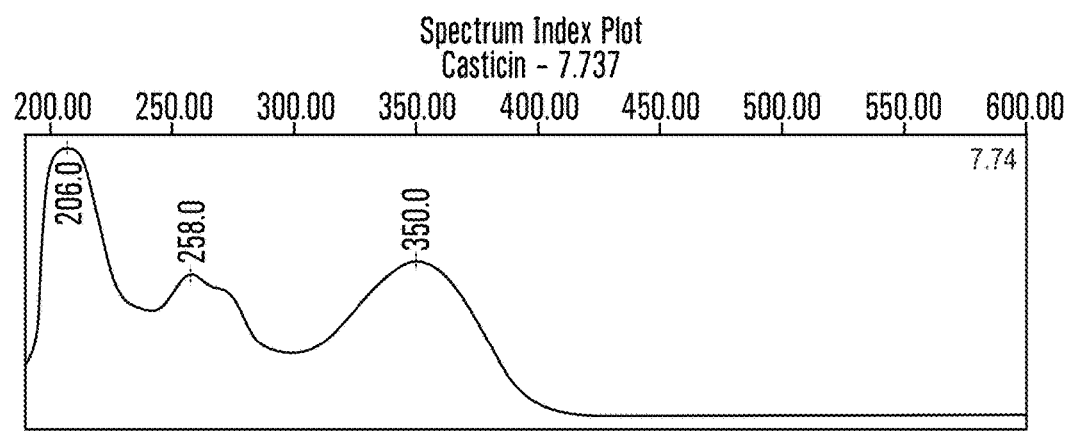
FIG. 10 shows a DAD spectrum of purified casticin after TMB as described in Example 3.
Figure 11:
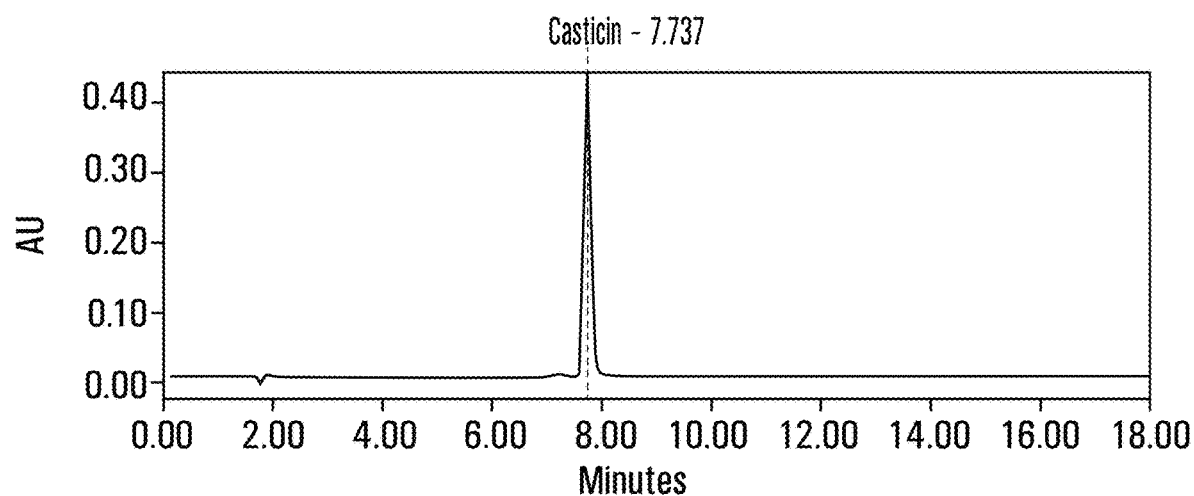
FIG. 11 shows HPLC chromatogram of purified casticin after TMB in Example 3.

True Moving Bed Purification Step 2 for Pre-enrichment: DAD spectrum (see FIG. 10) and HPLC chromatogram (see FIG. 11), purified casticin after TMB Content of casticin: 98.3% (m/m)

Figure 12:
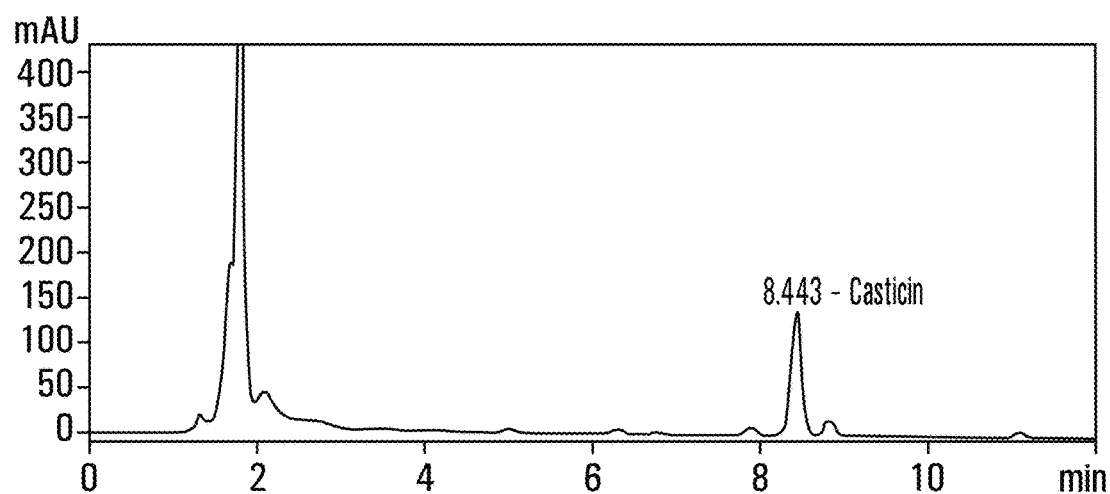
FIG. 12 shows an HPLC chromatogram of the starting product Essi Agni casti as described in Example 3.

HPLC chromatogram of the starting product Essi Agni casti (see FIG. 12):

Content of casticin in the dry extract: 0.145% (m/m)

Solvent system: n-heptane/ethyl acetate/ethanol/water (7:10:7:10) (v/v/v/v)

EXAMPLE 4

Purification of Chamazulene

Figure 13:
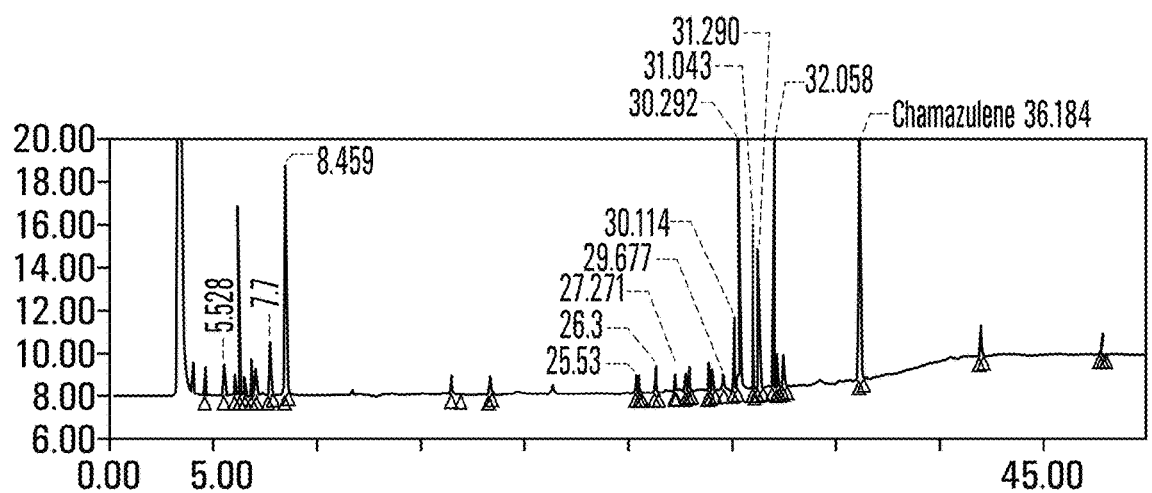
FIG. 13 shows a GC chromatogram of the starting product oleum chamomillae as described in Example 4.

GC chromatogram of the starting product oleum chamomillae (see FIG. 13):

Content of chamazulene in essential oil: 15.8% (m/m)

Figure 14:
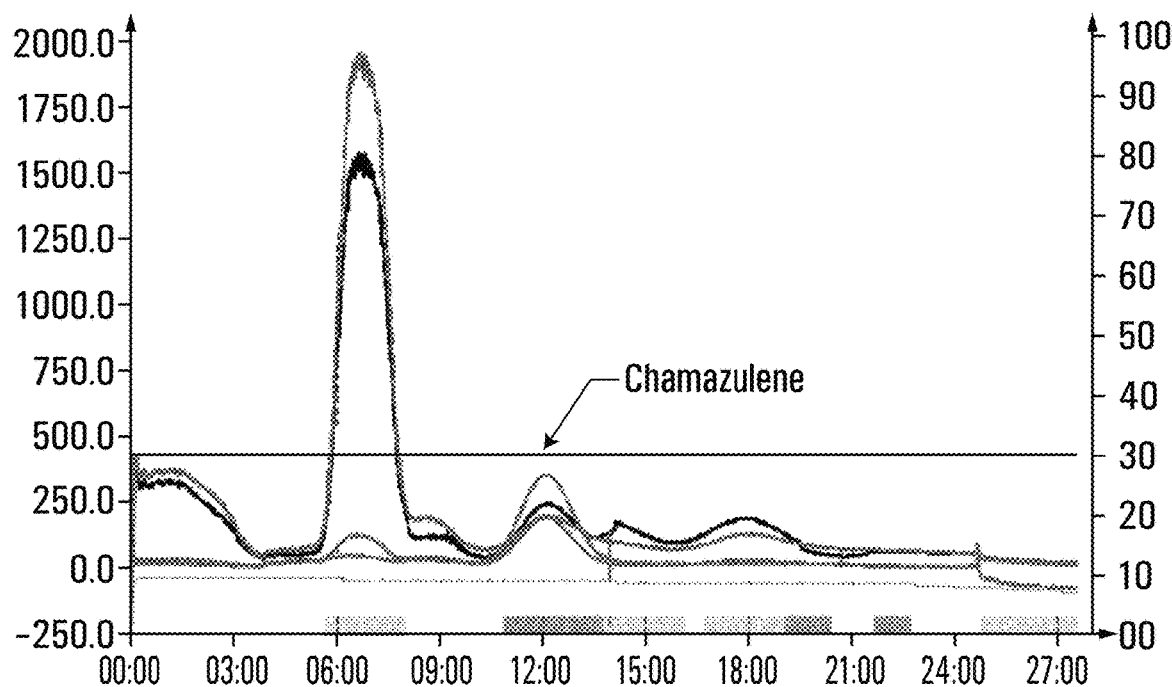
FIG. 14 shows the Batch partition chromatography (CPC) as described in Example 4.

Batch partition chromatography (CPC) (see FIG. 14):

Separation of 0.5 g oleum chamomillae in batch operation with n-heptane/TBME/acetonitrile (4:2:4)—the blue lines describe the separations in the later continuous partition chromatography.

Chamazulene 1. TMB step

Parameters:

| Rotation: | 2,600 rpm |
|---|---|
| Ascending mode: | |
| Flow rate elution: | 15 mL/min |
| Flow rate injection: | 5 mL/min |
| Pump duration: | 90 sec. |
| Descending mode: | |
| Flow rate elution: | 15 mL/min |
| Flow rate injection: | 5 mL/min |
| Pump duration: | 75 sec. |

Solvent system: n-heptane/TBME/acetonitrile (4:2:4) (v/v/v)

Figure 15:
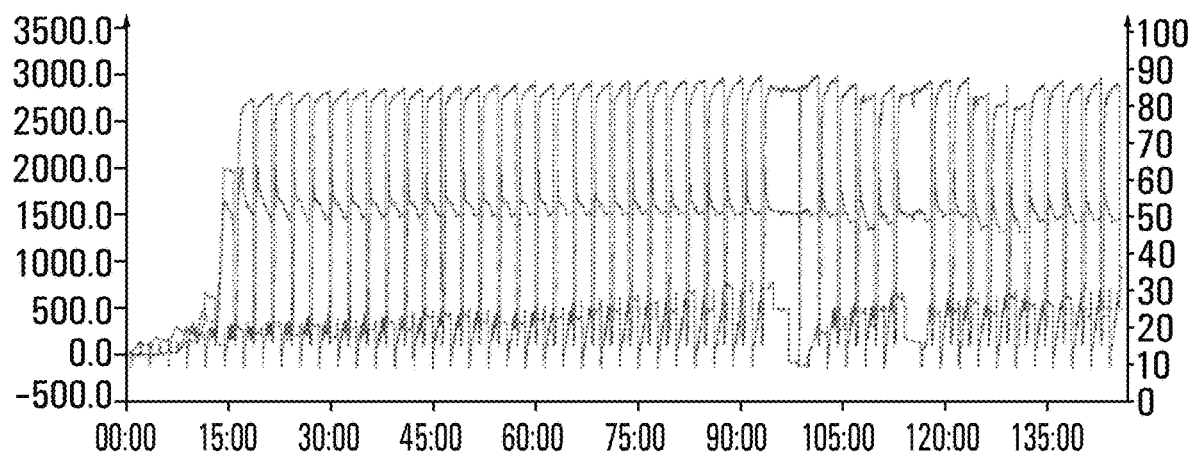
FIG. 15 shows a chromatogram for TMB Purification Step 1 Continuous Partition Chromatography (sCPC) as described in Example 4.

1. TMB Step Continuous Partition Chromatography (sCPC) (see FIG. 15):

Separation of oleum chamomillae (25 g/L) in continuous operation with the sCPC with n-heptane/ethyl acetate/ethanol/water (7:10:7:10) as Purification Step 1

Content of chamazulene after pre-enrichment TMB1: 70.3% (m/m)

2. TMB step

Parameters:

| Rotation: | 2,600 rpm |
|---|---|
| Ascending mode: | |
| Flow rate elution: | 15 mL/min |
| Flow rate injection: | 5 mL/min |
| Pump duration: | 30 sec. |
| Descending mode: | |
| Flow rate elution: | 15 mL/min |
| Flow rate injection: | 5 mL/min |
| Pump duration: | 60 sec. |

Solvent system: n-heptane/TBME/acetonitrile (4:2:4) (v/v/v)

Figure 16:
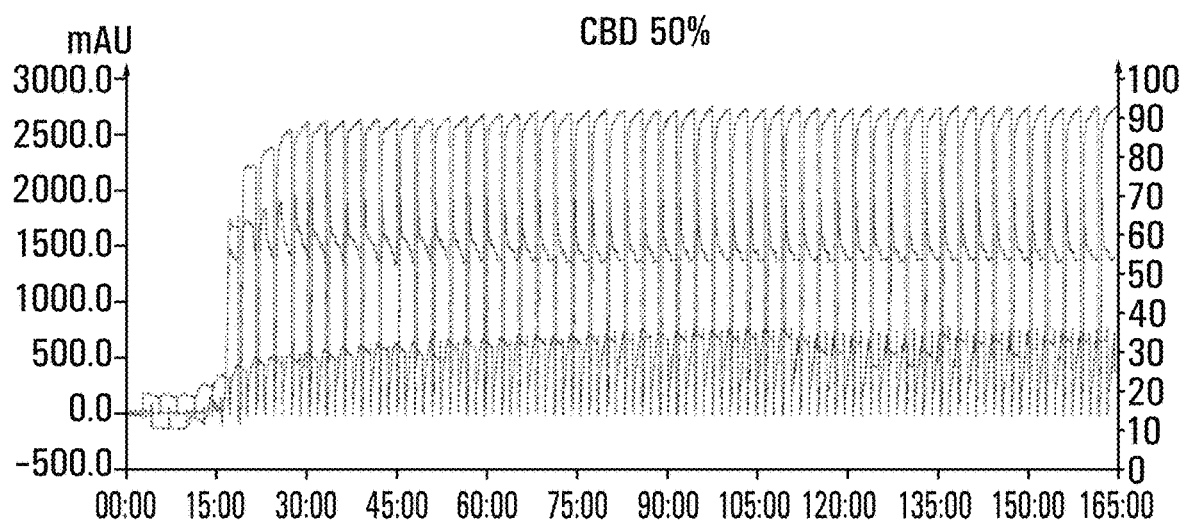
FIG. 16 shows a chromatogram for TMB Purification Step 2 Continuous Partition Chromatography (sCPC) as described in Example 4.

2. TMB Step Continuous Partition Chromatography (sCPC) (see FIG. 16):

Separation of the material from TMB Step 1 (25 g/L) in continuous operation with the sCPC with n-heptane/TBME/acetonitrile (4:2:4) as Purification Step 2.

Figure 17:
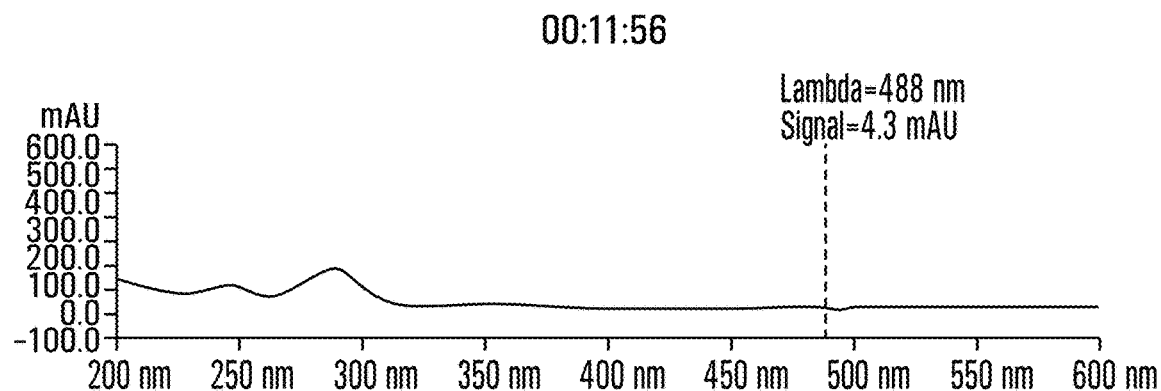
FIG. 17 shows a DAD spectrum of purified chamazulene after TMB Purification Step 2 as described in Example 4.
Figure 18:
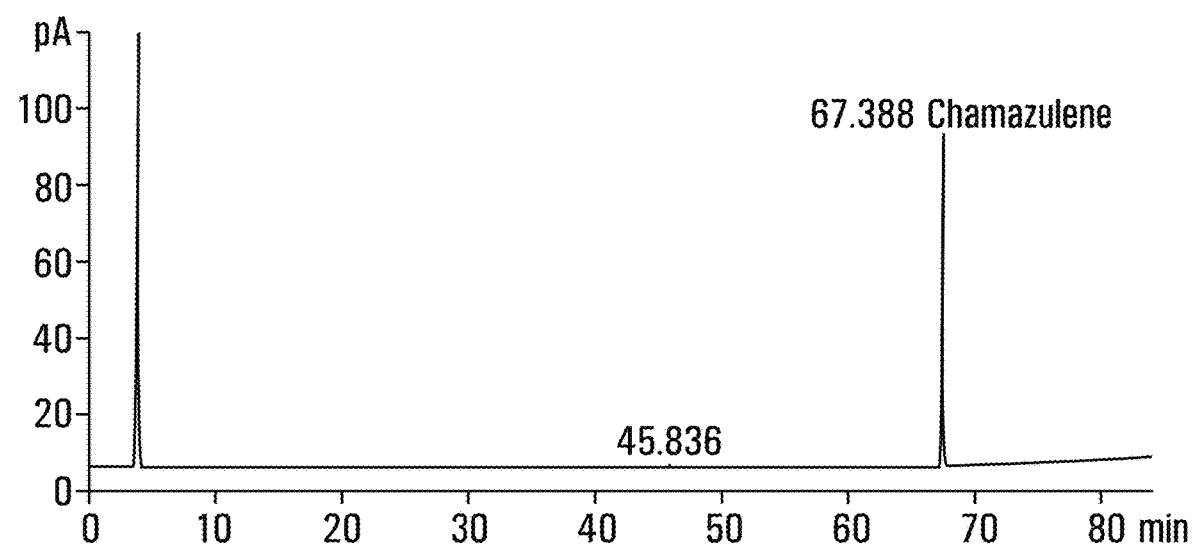
FIG. 18 shows a GC chromatogram of purified chamazulene after TMB Purification Step 2 as described in Example 4.

DAD spectrum (see FIG. 17) and GC chromatogram (see FIG. 18) purified chamazulene after TMB Purification Step 2:

Content of chamazulene: 99.0% (m/m)

EXAMPLE 5

Purification of Primulasaponins

Essi *Primula veris*

Content of primulasaponin 1 in the extract: ~20% (m/m)

Figure 19:
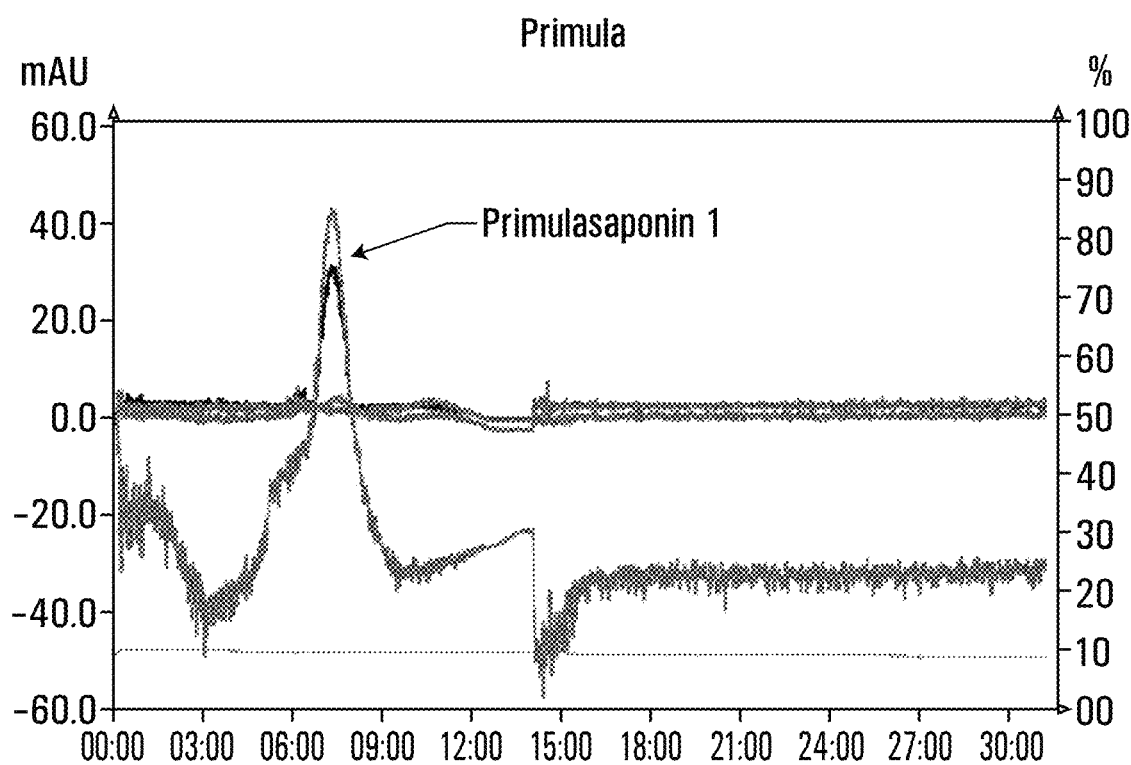
FIG. 19 shows the Batch partition chromatography (CPC) as described in Example 5.

Batch partition chromatography (CPC) (see FIG. 19):

Separation of 0.1 g Essi *Primula veris* in batch operation with n-heptane/ethyl acetate/water (6:5:4)—the blue lines describe the separations in the later continuous partition chromatography 1. TMB step Parameters:

| Rotation: | 2,600 rpm |
|---|---|
| Ascending mode: | |
| Flow rate elution: | 15 mL/min |
| Flow rate injection: | 5 mL/min |
| Pump duration: | 90 sec. |
| Descending mode: | |
| Flow rate elution: | 15 mL/min |
| Flow rate injection: | 5 mL/min |
| Pump duration: | 75 sec. |

Figure 20:
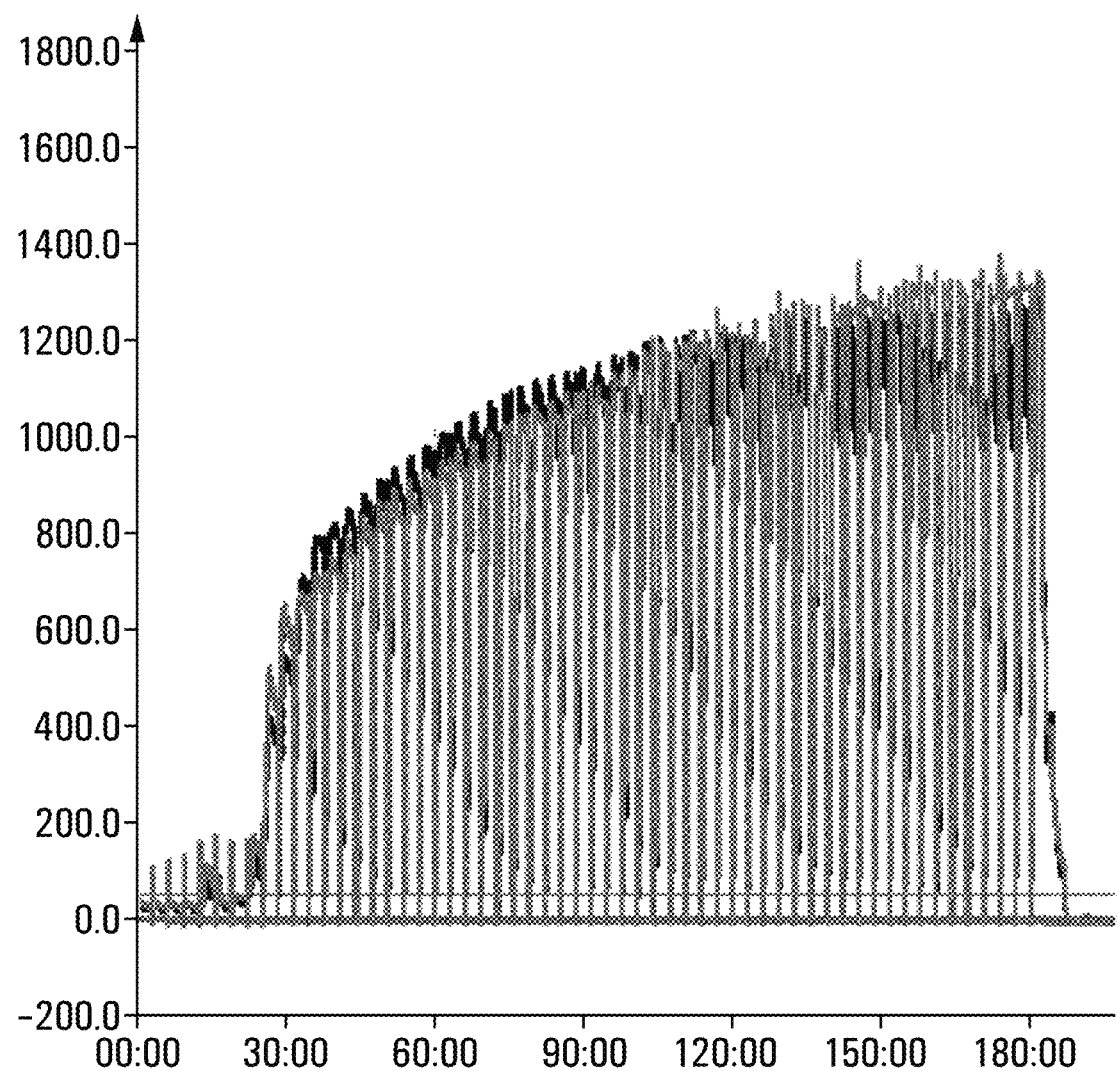
FIG. 20 shows a chromatogram for TMB Purification Step 1 Continuous Partition Chromatography (sCPC) as described in Example 5.

Solvent system: n-heptane/ethyl acetate/water (6:5:4) (v/v/v) 1. TMB Step Continuous Partition Chromatography (sCPC) (see FIG. 20):

Separation of Essi *Primula veris* (5 g/L) in continuous operation with the sCPC with n-heptane/ethyl acetate/water (6:5:4) as Purification Step 1

Content of primulasaponin 1 after pre-enrichment TMB1: 60.1% (m/m)

2. TMB step
Parameters:

| Rotation: | 2,600 rpm |
|---|---|
| Ascending mode: | |
| Flow rate elution: | 15 mL/min |
| Flow rate injection: | 5 mL/min |
| Pump duration: | 30 sec. |
| Descending mode: | |
| Flow rate elution: | 15 mL/min |
| Flow rate injection: | 5 mL/min |
| Pump duration: | 60 sec. |

Solvent system: n-heptane/ethyl acetate/water (6:5:4) (v/v/v)

Figure 21:
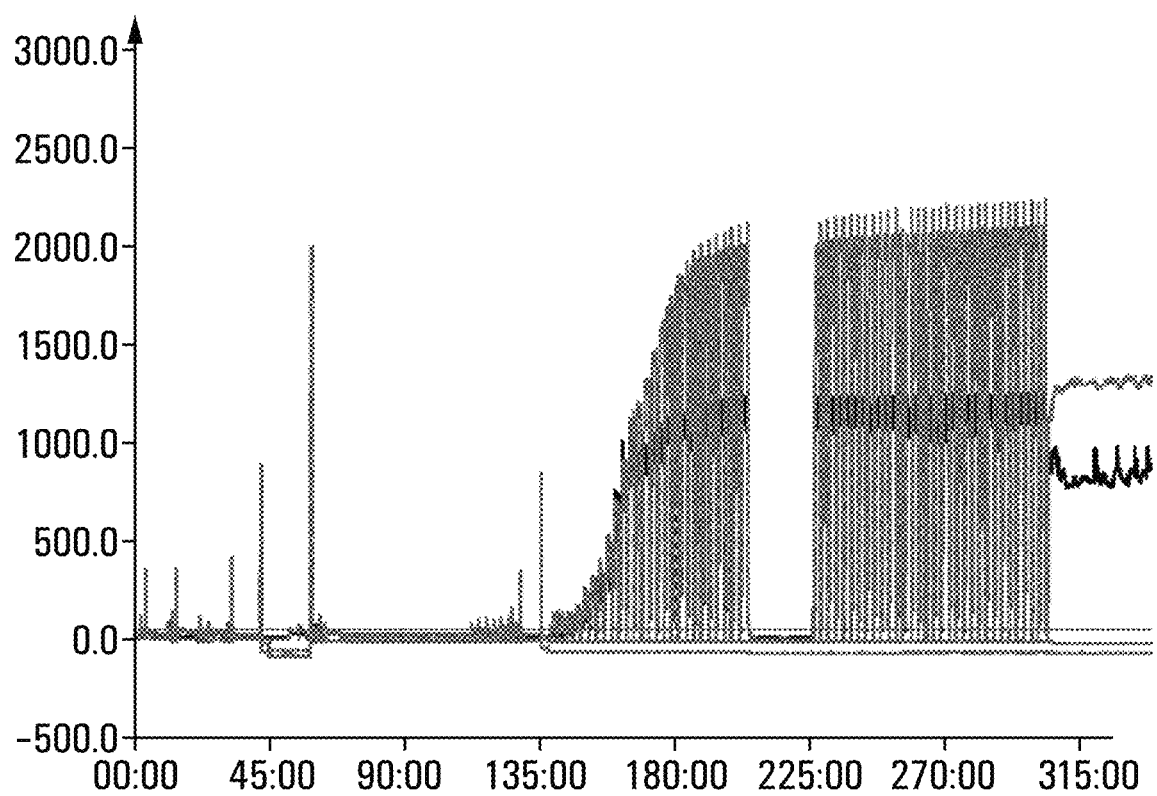
FIG. 21 shows a chromatogram for TMB Purification Step 2 Continuous Partition Chromatography (sCPC) as described in Example 5.

2. TMB Step Continuous Partition Chromatography (sCPC) (see FIG. 21):

Separation of the material from TMB step 1 (5 g/L) in continuous operation with the sCPC with n-heptane/ethyl acetate/water (6:5:4) as Purification Step 2

Figure 22:
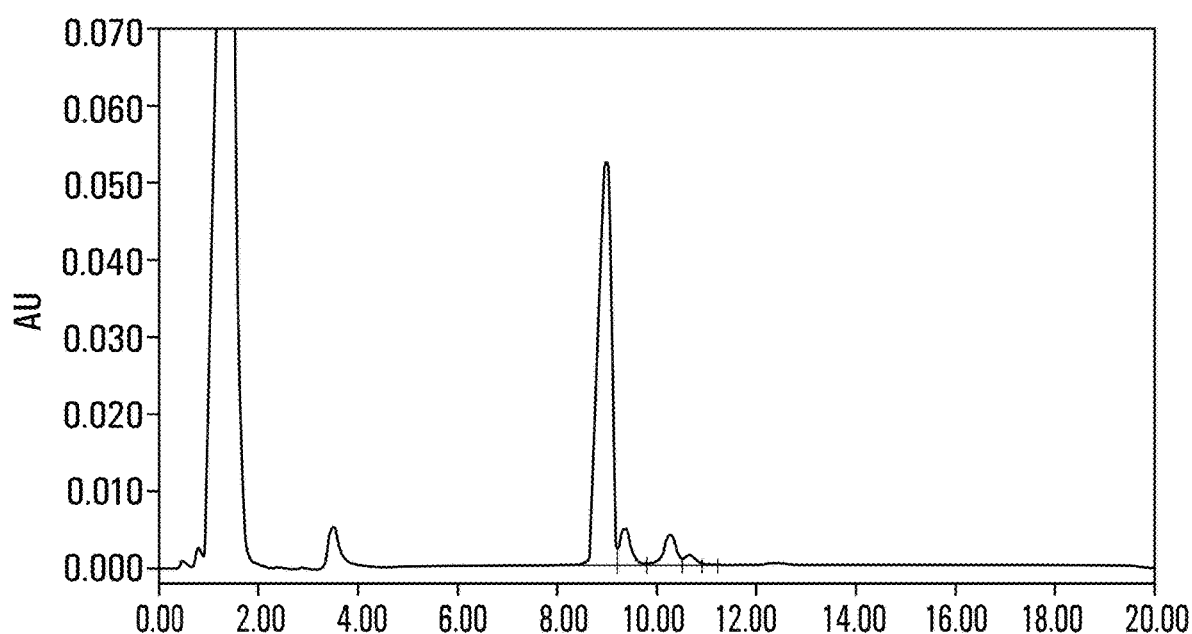
FIG. 22 shows an HPLC chromatogram of purified primulasaponin 1 after TMB Purification Step 2 as described in Example 5.

HPLC chromatogram purified primulasaponin 1 after TMB Purification Step 2 (see FIG. 22):

Content of primulasaponin 1: 84.0% (m/m)

The invention claimed is:

1. A method for separating and/or purifying one or more cannabinoids from a *Cannabis* plant extract, comprising a step of performing at least one liquid-liquid partition chromatography on the *Cannabis* plant extract to separate and/or purify the one or more cannabinoids, wherein in performing the at least one liquid-liquid partition chromatography a continuous change of the stationary phase to the mobile phase and vice versa takes place, and wherein one or more fractions are removed to separate and/or purify the one or more cannabinoids.

2. The method according to claim 1, wherein at least one rotor is used.

3. The method according to claim 2, wherein a rotation of more than 2,000 rpm takes place.

4. The method according to claim 1, wherein the *Cannabis* plant extract contains less than 40 wt % fat/lipids.

5. The method according to claim 1, wherein the *Cannabis* plant extract is obtained from a first solvent selected from the group consisting of alcohols, water, hydrocarbons, and mixtures thereof, and the soluble parts are used.

6. The method according to claim 1, wherein the *Cannabis* plant extract is a *Cannabis sativa* extract.

7. The method according to claim 1, wherein the stationary phase and mobile phase are independently selected from the group consisting of hydrocarbons having 5-8 carbon atoms, acetonitrile, ethyl acetate, t-butyl methyl ether, alcohols, and water, so that a two-phase system can be obtained.

8. The method according to claim 7, wherein the solvents at least contain:
 a.) n-heptane and/or acetonitrile, n-heptane/acetonitrile;
 b.) n-heptane/ethyl acetate/acetonitrile;
 c.) n-heptane/ethyl acetate/t-butyl methyl ether/acetonitrile;
 d.) n-heptane/ethyl acetate/methanol/water;
 e.) n-heptane/ethanol/water.

9. The method according to claim 7, wherein the stationary phase and mobile phase are independently selected from n-heptane, acetonitrile, ethyl acetate, t-butyl methyl ether, water, ethanol, methanol, n-heptane and/or acetonitrile, so that a two-phase system can be obtained.

10. A method for separating and/or purifying one or more cannabinoids from a *Cannabis* plant extract, comprising at least one liquid-liquid partition chromatography step, wherein a continuous change of the stationary phase to the mobile phase and vice versa takes place, wherein at least one cannabinoid is removed.

11. The method according to claim 10, wherein at least one rotor is used.

12. The method according to claim 11, wherein a rotation of more than 2,000 rpm takes place.

13. The method according to claim 10, wherein the *Cannabis* plant extract contains less than 40 wt % fat/lipids.

14. The method according to claim 10, wherein the *Cannabis* plant extract is obtained from a first solvent selected from the group consisting of alcohols, water, hydrocarbons, and mixtures thereof, and the soluble parts are used.

15. The method according to claim 10, wherein the one or more cannabinoids is cannabidiol or tetrahydrocannabinol.

16. The method according to claim 7, wherein the *Cannabis* plant extract is a *Cannabis sativa* extract.

17. The method according to claim 10, wherein the stationary phase and mobile phase are independently selected from the group consisting of hydrocarbons having 5-8 carbon atoms, acetonitrile, ethyl acetate, t-butyl methyl ether, alcohols, and water, so that a two-phase system can be obtained.

18. The method according to claim 10, wherein the solvents at least contain:
 a.) n-heptane and/or acetonitrile, n-heptane/acetonitrile;
 b.) n-heptane/ethyl acetate/acetonitrile;
 c.) n-heptane/ethyl acetate/t-butyl methyl ether/acetonitrile;
 d.) n-heptane/ethyl acetate/methanol/water;
 e.) n-heptane/ethanol/water.

19. The method according to claim 17, wherein the stationary phase and mobile phase are selected from n-heptane, acetonitrile, ethyl acetate, t-butyl methyl ether, water, ethanol, methanol, n-heptane and/or acetonitrile, so that a two-phase system can be obtained.

* * * * *

UNITED STATES PATENT AND TRADEMARK OFFICE
CERTIFICATE OF CORRECTION

| | |
|---|---|
| PATENT NO. | : 11,306,116 B2 |
| APPLICATION NO. | : 16/613546 |
| DATED | : April 19, 2022 |
| INVENTOR(S) | : Michael Englert and Andreas Rutz |

It is certified that error appears in the above-identified patent and that said Letters Patent is hereby corrected as shown below:

On the Title Page

(72) Inventors, please delete "Andreas Ruiz, Dornhausen (DE)" and insert -- Andreas Rutz, Dornhausen (DE) --

In the Claims

In Column 10, Line 42, Claim 16, please delete "The method according to claim 7, wherein the *Can-*" and insert -- The method according to claim 10, wherein the *Can-* --

Signed and Sealed this
Fourteenth Day of June, 2022

Katherine Kelly Vidal
*Director of the United States Patent and Trademark Office*